(12) United States Patent
Mohammed et al.

(10) Patent No.: US 11,970,741 B1
(45) Date of Patent: Apr. 30, 2024

(54) GENETIC SEX-DETERMINATION METHOD

(71) Applicant: KING FAISAL UNIVERSITY, Al-Ahsa (SA)

(72) Inventors: Mohei Eldin Soliman Mohammed, Al-Ahsa (SA); Heba Allah A. Mohasseb, Al-Ahsa (SA); Mohammed M. BA Abdullah, Al-Ahsa (SA); Hany S. Elbarbary, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/306,023

(22) Filed: Apr. 24, 2023

(51) Int. Cl.
*C12Q 1/6879* (2018.01)
*C12Q 1/686* (2018.01)

(52) U.S. Cl.
CPC ........... *C12Q 1/6879* (2013.01); *C12Q 1/686* (2013.01); *C12Q 2600/158* (2013.01)

(58) Field of Classification Search
CPC ............................ C12Q 1/6789; C12Q 1/6879
See application file for complete search history.

(56) References Cited

U.S. PATENT DOCUMENTS

| 2016/0138119 A1* | 5/2016 | Solliman | C12Q 1/6895 436/501 |
|---|---|---|---|
| 2020/0329685 A1 | 10/2020 | Qimron et al. | |

OTHER PUBLICATIONS

GenBank Accession No. MK991776, Simmondsia chinensis sex-determining region Y protein-like gene (Year: 2020).*
GenBank Accession No. AF000024, Carica papaya sex-determining region Y protein (SRY) gene (Year: 2020).*
GenBank Accession No. KC577225, Phoenix dactylifera SRY protein-like gene (Year: 2014).*
Parasnis et al. "A highly reliable sex diagnostic PCR assay for mass screening of papaya seedlings." Molecular Breeding 6 (2000):337-344. (Year: 2000).*
Solliman et al. Identification and sequencing of Date-SRY Gene: A novel tool for sex determination of date palm (*Phoenix dactylifera* L.). Saudi J Biol Sci. Mar. 2019;26(3):514-523. doi: 10.1016/j.sjbs. 2017.08.002. Epub Aug. 16, 2017. PMID: 30899166; PMCID: PMC6410340 (Year: 2017).*
Solliman et al. Identification and sequencing of Date-SRY Gene: A novel tool for sex determination of date palm (*Phoenix dactylifera* L.). Saudi J Biol Sci.;26(3) :514-523. doi: 10.1016/j.sjbs.2017.08. 002. Epub Aug. 16, 2017; cited as NPL#6, on IDS filed Apr. 24, 2023 (Year: 2017).*
Mohei El-Din Solliman et al., "Discovery of the human homolog of sex-determining region (SRY) gene in dioecious plants," Saudi Journal of Biological Sciences, vol. 30, Issue 2, Feb. 2023, 103548.
Bechkri et al., "Intérêt de la recherche du gène SRY dans le syndrome de turner dans la region de Constantine," Mémoire présenté en vue de l'obtention du diplôme de Master, Freres Mentouri Constantine I University, Jun. 20, 2022.
Nada et al., "Intérêt de la recherche du gène SRY dans l'ambiguïté sexuelle," Freres Mentouri Constantine I University, Jul. 15, 2021.
Cronk et al., "Default Sex and Single Gene Sex Determination in Dioecious Plants," Front. Plant Sci., Jul. 29, 2020, Sec. Plant Development and EvoDevo vol. 11—2020.
Montalvao et al., "The Diversity and Dynamics of Sex Determination in Dioecious Plants," Front Plant Sci. 2020; 11:580488.
Mohei El-Din Solliman et al., "Identification and sequencing of Date-SRY Gene: A novel tool for sex determination of date palm (*Phoenix dactylifera* L.)," Saudi J Biol Sci., Mar. 2019; 26(3):514-523.
Mohei El-Din Solliman et al., "A new reliable and sensitive PCR assay as an early diagnosis for Sex-determination in Jojoba plants based on the human SRY gene," Research Square, May 13, 2022.
Mohei El-Din Solliman et al., "Karyotypic and Cytogenetic Analysis for Jojoba Plants and Early Diagnosis of Sex in Jojoba by Amplifications of SRY Gene as Direct Link to Sex Determination Chromosome," Plant Cell Biotechnology and Molecular Biology, vol. 22, Issue 69-70, p. 129-140, Dec. 2, 2021.

* cited by examiner

*Primary Examiner* — Aaron A Priest
*Assistant Examiner* — Tian NMN Yu
(74) *Attorney, Agent, or Firm* — Nath, Goldberg & Meyer; Richard C. Litman

(57) ABSTRACT

A sex-determination method for a dioecious plant includes obtaining a sample of a dioecious plant and determining a presence or absence of SEQ ID NO: 2 in the sample. The presence of SEQ ID NO: 2 in the sample is indicative that the sample is from a male dioecious plant. Using the sex determination method for a dioecious plant, the sex of dioecious plants may even be determined when the dioecious plants are still young, i.e., when they are seedlings.

8 Claims, 1 Drawing Sheet

Specification includes a Sequence Listing.

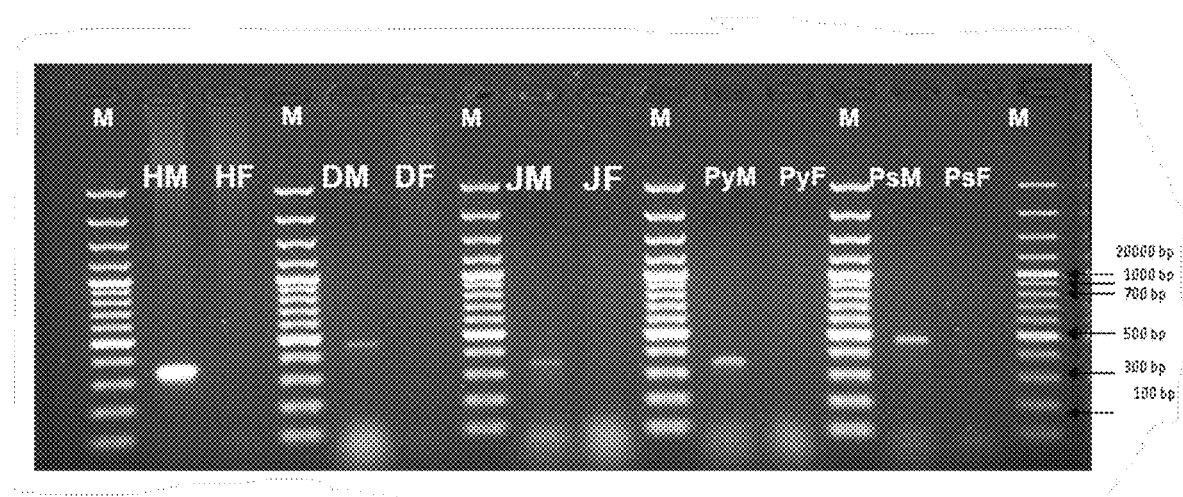

GENETIC SEX-DETERMINATION METHOD

The Applicants hereby incorporate by reference the sequence listing contained in the XML file titled SOLLIMAN_ET_AL.xml, created Apr. 10, 2023 and having 8,896 bytes of data.

BACKGROUND OF THE INVENTION

1. Field of the Invention

The present subject matter relates to a sex determination method, and particularly to a genetic sex determination for dioecious plants based on the identification of the SRY gene.

2. Description of the Related Art

Dioecious plants have separate male and female plants. Sex determination in the early developmental stages of dioecious crops, for example, jojoba, date palm, papaya, and pistachios, is economically beneficial as only the female plants bear fruit. While the male plants may be useful as pollinators, dioecious plants are entirely pollinated manually in both traditional oasis horticulture and in modern commercial orchards. As such, many date breeders and growers find little use in maintaining male plants. Thus, once the sex of the plant is determined, many breeders and growers proceed to maintain only the female plants. The earliest point, however, at which male and female trees can be distinguished by external morphology is when the plant flowers, usually 5-8 years after planting.

Accordingly, a method of determining the sex of the plant at an earlier stage, e.g., the seedling stage, would avoid the need to invest time and expense in growing and maintaining unwanted male plants, thereby solving the aforementioned problems.

SUMMARY OF THE INVENTION

The present subject matter relates to a sex-determination method for a dioecious plant, comprising: obtaining a sample from a dioecious plant; and determining a presence or absence of a fragment of a dioecious SRY gene (SEQ ID NO: 2) in the sample, whereby the presence of SEQ ID NO: 2 in the sample is indicative that the sex of the dioecious plant is male.

In an embodiment, the present subject matter relates to a sex-determination method for a dioecious plant, which may include obtaining a sample from a dioecious plant, extracting a nucleic acid from the sample, contacting under amplification conditions the nucleic acid from the sample with a male-specific SRY primer pair selected from a first primer pair and a second primer pair, detecting the presence or absence of amplification products. and determining a presence or absence of SEQ ID NO: 2, whereby the presence of SEQ ID NO: 2 in the sample indicates that the plant is a male dioecious plant. In an embodiment, the presence of amplicons indicates the presence of SEQ ID NO: 2.

In an embodiment, the first primer pair includes an oligonucleotide including SEQ ID NO: 3 and an oligonucleotide including SEQ ID NO: 8. In an embodiment, the second primer pair includes an oligonucleotide including SEQ ID NO: 4 and an oligonucleotide including SEQ ID NO: 5. In an embodiment, the third primer pair includes an oligonucleotide including SEQ ID NO: 6 and an oligonucleotide including SEQ ID NO: 7.

The presence of SEQ ID NO: 2 in the sample is indicative that the sample is from a male dioecious plant. Using the sex determination method for a dioecious plant, the sex of dioecious plants may be determined when the dioecious plants are still young, i.e., prior to flowering of the plants.

Also provided are kits for sex determination of a dioecious plant.

These and other features of the present subject matter will become readily apparent upon further review of the following specification and drawings.

BRIEF DESCRIPTION OF THE DRAWINGS

The sole drawing FIGURE, FIG. 1, is a gel electrophoresis image obtained of PCR amplification products resulting from screening for the presence of SRY gene in human male (HM) and human female (HF) compared with different varieties of dioecious plants, including dates (DM and DF), jojoba (JM and JF), papaya (PyM and PyF) and Pistachios (PsM and PsF), using specific primers universal SryF1+ universal SryR1 lane M DNA 100 bp Marker.

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a sex-determination method for a dioecious plant. In an embodiment, the method may include obtaining a sample of a dioecious plant and determining a presence or absence of a dioecious SRY gene, or a fragment of a dioecious SRY gene, as represented by way of non-limiting example by the fragment of SEQ ID NO: 2, in the sample. In an embodiment, the dioecious plant is selected from the group consisting of jojoba, date palm, papaya, and pistachio. In an embodiment, the presence of SEQ ID NO. 2 in the sample is indicative that the sample is from a male dioecious plant. The sample may be obtained from any part of the dioecious plant at any stage of development of the dioecious plant. For example, the stage of development can be the seedling stage. In an embodiment, the sample may include but is not limited to plant tissue (including leaves, seeds, petals, flowers, bark, etc.), extracts of plant tissue, and/or plant body fluid. Thus, using the sex determination method for a dioecious plant, the sex of dioecious plants may even be determined when the dioecious plants are still young, i.e., when they are seedlings.

The SRY (sex determining region Y) gene is a gene typically associated with initiation of male sex determination in humans and is rarely discovered in plants. Similar to the XY-system of chromosomes in humans, the male dioecious SRY gene determines the gender of the offspring. Unlike humans, however, the sex chromosomes in the dioecious plant are homomorphic. The present methods for sex-determination of a dioecious plant are based on the surprising discovery of the SRY gene for dioecious plants (SEQ ID NO: 1) herein, "dioecious SRY gene". SEQ ID NO: 2 has been further identified as a fragment of the SRY gene (SEQ ID NO: 1) which corresponds exactly to a fragment of the human SRY gene. As such, it should be understood that the primer pairs described herein can also be used for genetic sex determination of humans.

Based on the present discovery, the sex of a dioecious plant may be genetically determined by determining a presence or absence of SEQ ID NO: 2 in a dioecious plant sample. In an embodiment, determining a presence or absence of SEQ ID NO: 2 in the dioecious plant sample may be carried out by extracting nucleic acids from the sample, contacting under amplification conditions the nucleic acid from the sample with a male-specific dioecious SRY primer pair, and detecting the presence or absence of amplification products or amplicons. The presence of amplification products may indicate the presence of the male-specific SRY gene in the dioecious plant, i.e., that the sample is from a male plant. The absence of amplification products may indicate that the sample is from a female plant. Other suitable methods for determining a presence or absence of SEQ ID NO: 2 in the dioecious plant sample are further contemplated herein.

As discussed above, the nucleic acid extracted from the sample may be subjected to amplification conditions using male-specific SRY primer pairs. The male-specific SRY primer pairs may include primers specific for amplification of SEQ ID NO: 2. For example, the male-specific SRY primer pair may include an oligonucleotide primer including SEQ ID NO: 3 and an oligonucleotide primer including SEQ ID NO: 8, or may include an oligonucleotide primer including SEQ ID NO: 4 and an oligonucleotide primer including SEQ ID NO: 5, or an oligonucleotide primer including SEQ ID NO: 6 and an oligonucleotide primer including SEQ ID NO: 7. The male-specific SRY primer pairs may include other primers specific for amplification of SEQ ID NO: 2. The presence of any amplification products may indicate the presence of a male-specific SRY gene in the dioecious plant, i.e., that the dioecious plant sample is from a male dioecious plant.

One method for contacting under amplification conditions the nucleic acid from the sample with a male-specific SRY primer pair may include subjecting the nucleic acid and the male-specific SRY primer pair to standard polymerase chain reaction (PCR) cycles. In an embodiment, the sex of different varieties of dioecious plants may be determined by conducting PCR screening for the presence of the SRY gene in different dioecious plants using a male-specific SRY primer pair. In this regard, FIG. 1 shows a gel electrophoresis image of PCR amplification products obtained for human female (HF), human male (HM) and different varieties of dioecious plants, where (M) is a DNA 1-KB Marker that was used. The male plants only show a single band on the gel electrophoresis. Thus, using PCR amplification technology, the sex of the plant can be identified. In this regard, as shown in FIG. 1, the dioecious plants subject to the present methods can include, by way of non-limiting example, dates (DM and DF), jojoba (JM and JF), papaya (PyM and PyF), and Pistachios (PsM and PsF).

The terms "nucleic acid" and "nucleic acid molecule" may be used interchangeably herein. The terms refer to a deoxyribonucleotide (DNA), ribonucleotide polymer (RNA), RNA/DNA hybrids and polyamide nucleic acids (PNAs) in either single- or double-stranded form, and unless otherwise limited, would encompass known analogs of natural nucleotides that can function in a similar manner as naturally occurring nucleotides.

Nucleic acid extracted from the sample may be isolated using known methods. Nucleic acid can be isolated using, for example, Plant DNAzol Reagent from Life Technologies now Invitrogen (Invitrogen Life Technologies), or DNeasy Mini-Kit (Qiagen). An isolated DNA sequence, for example, is substantially separated or purified away from other nucleic acid sequences with which the nucleic acid is normally associated in the cell of the organism in which the nucleic acid naturally occurs i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids. The term "substantially purified", as used herein, refers to a molecule separated from other molecules normally associated with it in its native state. More preferably, a substantially purified molecule is the predominant species present in a preparation. A substantially purified molecule may be greater than 60% free, greater than 75% free, or greater than 90% free from the other molecules (exclusive of solvent) present in the natural mixture. The term "substantially purified" is not intended to encompass molecules present in their native state.

It should be understood that any suitable technique for extracting and/or isolating nucleic acids from biological samples that is known in the art may be used to extract nucleic acids and/or isolate nucleic acids from the dioecious plant sample.

As is known in the art, PCR means a reaction for the in vitro amplification of a specific target nucleic acid sequence and is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. The reaction is cycled through different temperatures optimized for each step in a thermal cycler instrument. Particular temperatures, durations at each step, and rates of change between steps depend on many factors well known to those of ordinary skill in the art.

The term "PCR" further encompasses derivative forms of the reaction, including but not limited to, RT-PCR, real-time PCR, nested PCR, quantitative PCR, multiplexed PCR, and the like. "Reverse transcription PCR" or "RT-PCR" indicates a PCR that is preceded by a reverse transcription reaction that converts a target RNA to a complementary single stranded DNA, which is then amplified. For example, where RNA nucleic acid species may be used for detection of certain nucleotide sequences, a DNA copy (cDNA) of the RNA transcripts of interest can be synthesized prior to the amplification step. The cDNA copy can be synthesized by reverse transcription, which may be carried out as a separate step, or in a homogeneous reverse transcription-polymerase chain reaction, a modification of the polymerase chain reaction for amplifying RNA. "Real-time PCR" means a PCR for which the amount of reaction product, i.e. the amplicon or amplification product, is monitored as the reaction proceeds. There are many forms of real-time PCR that differ mainly in the detection chemistries used for monitoring the reaction product. "Nested PCR" means a two-stage PCR wherein the amplicon of a first PCR becomes the sample for a second PCR using a new set of primers, at least one of which binds to an interior location of the first amplicon. "Multiplexed PCR" means a PCR wherein multiple target sequences (or a single target sequence and one or more reference sequences) are simultaneously carried out in the same reaction mixture.

Any other suitable method for polynucleotide amplification that is well known to one of ordinary skill in the art may be employed. Other amplification methods may include for example, ligase chain reaction ("LCR") and rolling circle amplification ("RCA").

Any well-known methods for detection of amplification products may be employed. In some embodiments, the detection step can comprise gel electrophoresis, capillary electrophoresis, fluorescence resonant energy transfer (FRET), or hybridization to a labeled probe, such as a probe labeled with biotin, a fluorescent moiety, an antigen, a molecular weight tag, radioactive label, or other detectable modification. In some embodiments, the detection step can comprise the incorporation of a label (such as but not limited to fluorescent or radioactive labels) during an extension reaction. The detection step can further comprise measuring fluorescence, mass, charge, and/or chemiluminescence.

Real-time detection of the amplification products may be performed. Real-time detection in the context of amplification indicates an amplification reaction for which the amount of reaction product, i.e., the amplicon or amplification product, is monitored simultaneously with the reaction progression. Amplification products are monitored and quantitated as the amplification products are generated in the reaction mixture. Examples of real-time detection include RT-PCR (real-time polymerase chain reaction) and real-time quantitative PCR).

TaqMan PCR probes may be the basis for detection of the amplification products. TaqMan probes were developed by Applied Biosystems for use with real-time PCR reactions and are commercially available from Applied Biosystems. TaqMan probes comprise an oligonucleotide sequence containing a fluorophore covalently attached to the 5'-end of the oligonucleotide probe and a quencher at the 3'-end. Several different fluorophores (including. 6-carboxyfluorescein (FAM) or tetrachlorofluorescein (TET) and quenchers (e.g., tetramethylrhodamine (TAMRA) or dihydrocyclopyrroloindole tripeptide minor groove binder (MGB)) are available for inclusion in TaqMan probes. The quencher molecule quenches the fluorescence emitted by the fluorophore when excited by an appropriate light source via FRET (Fluorescence Resonance Energy Transfer). Upon extension of the TaqMan probes by Taq polymerase, the 5' to 3' exonuclease activity of the polymerase induces release of the fluorophore and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

In addition to the TaqMan fluorescent probes, other fluorescent probes may be used for detection of the amplification products. Fluorophores that may be used for fluorescent probes include but are not limited to DAPI (4',6-dismidino- 2-phylindole; FITC (fluorescein isothiocyanate), DiI (1,1'-dihexyl-3,3,3',3'-tetramethlindocarbocyanine perchlorate), BODIPY FL and CY3, as well as any others commonly known to one of skill in the art.

Determining a presence or absence of SEQ ID NO: 2 in the dioecious plant sample may include detecting a protein encoded by SEQ ID NO: 2 using, e.g., an enzyme-linked immunosorbent assay (ELISA). The ELISA may be a direct ELISA in which antibodies to the protein are produced, conjugated with enzymes, and applied directly to the sample prepared for testing. Detection of a binding complex between the protein and the antibody indicates the presence of SEQ ID NO: 2. Preparation of antibodies and the extract from the sample for use in the ELISA can be conducted in any suitable manner known in the art.

Also provided are kits for sex determination of a dioecious plant. A kit for sex determination of a dioecious plant may include one or more pairs of male-specific SRY primers and non-specific amplification reagents for amplifying the SRY gene. The male-specific SRY primer pairs may include SEQ ID NO: 3 and SEQ ID NO: 8, SEQ ID NO: 4 and SEQ ID NO. 5 or SEQ ID NO: 6 and SEQ ID NO: 7. The kit may include a nucleic acid probe that binds to an amplified region of the SRY gene. The nucleic acid probe may be fluorescently labeled by any means known to one of ordinary skill in the art.

The kit for sex determination of a dioecious plants may include an ELISA kit for use in detecting the presence of a protein encoded by SEQ ID NO: 1 or SEQ ID NO: 2. The kit may include at least one antibody against the protein encoded by SEQ ID NO: 1 or SEQ ID NO: 2 and at least one indicator to detect a binding complex of the protein encoded by SEQ ID NO: 1 or SEQ ID NO: 2 and the at least one antibody.

The following examples are illustrative only, and are not intended to limit the present teachings.

EXAMPLES

Example 1

As shown in FIG. 1, PCR amplification for screening of the presence of SRY gene with human male (HM and HF) and female were compared with different varieties of dioecious plant (dates (DM and DF), jojoba (JM and JF), papaya (PyM and PyF) and Pistachios (PsM and PsF)) using specific primers universal SryF1+ universal SryR1 lane M DNA 100 bp Marker.

The specific primers used can be seen in the following Table 1.

TABLE 1

| Primer's name | sequences | SEQ ID NO: |
|---|---|---|
| SRY F1 | 3-TCTTGCGTGGGGCACTTACAGCAACTC-3 | SEQ ID NO: 3 |
| SRY R1 | 5'-GCTGGAGGCAAGCGCCATAATCTGAG-3'. | SEQ ID NO: 4 |
| SRYF2 | 5-GTGATCCTGAAGCTGGTTTCTTGAG-3 | SEQ ID NO: 5 |
| SRYR2 | 5-TCGCCTTCCGACTAGGTGAAGAG-3 | SEQ ID NO: 6 |

It is to be understood that the present teachings are not limited to the embodiments described above, but encompasses any and all embodiments within the scope of the following claims.

We claim:

1. A sex-determination method for a dioecious plant, comprising:

obtaining a sample from a dioecious plant; and determining a presence or absence of a dioecious SRY gene (SEQ ID NO: 2) in the sample, whereby the presence of SEQ ID NO: 2 in the sample is indicative that the sex of the dioecious plant is male; and wherein the dioecious plant is a papaya;

wherein determining a presence or absence of SEQ ID NO: 2 in the sample includes:

a) extracting nucleic acid from the dioecious plant sample;

b) contacting under amplification conditions the nucleic acid from the sample with a male-specific dioecious SRY primer pair; and c) detecting a presence or absence of amplification products, whereby the presence of amplification products is indicative of the presence of SEQ ID NO: 2 in the sample; and wherein the male-specific dioecious SRY primer pair is selected from the group consisting of an oligonucleotide including SEQ ID NO: 3 and an oligonucleotide including SEQ ID NO: 8, an oligonucleotide including SEQ ID NO: 4 and an oligonucleotide including SEQ ID NO: 5, and an oligonucleotide including SEQ ID NO: 6 and an oligonucleotide including SEQ ID NO: 7.

2. The sex-determination method for a dioecious plant according to claim 1, wherein the sample includes dioecious plant tissue or an extract from dioecious plant tissue.

3. The sex-determination method for a dioecious plant according to claim 2, wherein the dioecious plant tissue is selected from the group consisting of leaves, seeds, petals, flowers, and bark.

4. The sex-determination method for a dioecious plant according to claim 1, wherein the dioecious plant is a seedling.

5. The sex-determination method for a dioecious plant according to claim 1, further comprising isolating the nucleic acid extracted from the sample.

6. The sex-determination method for a dioecious plant according to claim 1, wherein the nucleic acid is DNA.

7. The sex-determination method for a dioecious plant according to claim 1, wherein the amplification conditions comprise conditions for carrying out a polymerase chain reaction (PCR).

8. A kit for sex determination of a papaya, comprising:
a pair of male-specific SRY primers; and amplification reagents for polymerase chain reaction (PCR) amplification of SEQ ID NO: 2;
wherein the male-specific SRY primer pair is selected from the group consisting of an oligonucleotide including SEQ ID NO: 4 and an oligonucleotide including SEQ ID NO: 5, and an oligonucleotide including SEQ ID NO: 6 and an oligonucleotide including SEQ ID NO: 7.

* * * * *

SEQUENCE LISTING

```
Sequence total quantity: 8
SEQ ID NO: 1            moltype = DNA   length = 914
FEATURE                 Location/Qualifiers
source                  1..914
                        mol_type = genomic DNA
                        organism = Phoenix dactylifera
SEQUENCE: 1
gggggatac cagttaccca aatcggccct ctaagtatct gtgcgcaacg gccagacatc  60
tttagaggcc acttctgcga ttcttgaagc gacccttgag agcattcatc gagtggtctc  120
cgtcctcacg cgtggatggc tctcgagatc ccccaatgcg acactctgag atcacctatc  180
gactgggata ccggtgataa aatgctcact ggagccaagg gatggacctt cttcccggag  240
gttcagagat ttcaggccat gcacataaat aaatgcacga gttataaata tccacctcct  300
ctgaaggcga aaatactgcc gaagacttgc agtttgcttc ccgctcatcc cgcttcgtta  360
ctctgcttcg aagtgcaaac tggacaacag gtaagcgggg gaaatggagg gaacagggta  420
tgcatagatt tcggagattc gaacaaattg gttggcactt tagggttata caatatatct  480
tttccgttat aagccttaat ggaaggaaag gtgggggaaa tccattttgg attgagaaat  540
cgatgtgccg gtgcttaact tataatccag attgaaactt cgtgttcgtg atcaggaccc  600
agcaccaaca ccagcgatgg gggcgggcga caataccacc atagcggttc tagtagcagc  660
aaaaaatagt ggcataacaa acataagtag tagaacatga gtagcagaag tttacccggc  720
gcaataaccg gtggcactag tagcagaagc ataggctttt tgggtaccgg gcagaggcaa  780
ggcatcgaat ccctcatcaa gcccatccac atcaatagct cactacccac caacatcgaa  840
ataagggat gagtcgactg gcgaatcagc tgcaataatt ggactcgacc agtgcaactg  900
gaacaacagg taaa                                                    914
```

| SEQ ID NO: 2 | moltype = DNA length = 365 |
| --- | --- |
| FEATURE | Location/Qualifiers |
| source | 1..365 |
| | mol_type = genomic DNA |
| | organism = Phoenix dactylifera |

SEQUENCE: 2
```
ctctaagtat cagtgtgaaa cgggagaaaa cagtaaaggc aacgtccagg atagagtgaa    60
gcgacccatg aacgcattca tcgtgtggtc tcgcgatcag aggcgcaaga tggctctaga   120
gaatcccaga atgcgaaact cagagatcag caagcagctg ggataccagt ggaaaatgct   180
tactgaagcc gaaaaatggc cattcttcca ggaggcacag aaattacagg ccatgcacag   240
agagaaatac ccgaattata agtatcgacc tcgtcggaag gcgaagatgc tgccgaagaa   300
ttgcagtttg cttcccgcag atcccgcttc ggtactctgc agcgaagtgc aactggacaa   360
caggt                                                               365
```

| SEQ ID NO: 3 | moltype = DNA length = 21 |
| --- | --- |
| FEATURE | Location/Qualifiers |
| source | 1..21 |
| | mol_type = other DNA |
| | organism = synthetic construct |

SEQUENCE: 3
```
agcagtcagg gaggcagatc a                                              21
```

| SEQ ID NO: 4 | moltype = DNA length = 27 |
| --- | --- |
| FEATURE | Location/Qualifiers |
| source | 1..27 |
| | mol_type = other DNA |
| | organism = synthetic construct |

SEQUENCE: 4
```
tcttgcgtgg ggcacttaca gcaactc                                        27
```

| SEQ ID NO: 5 | moltype = DNA length = 26 |
| --- | --- |
| FEATURE | Location/Qualifiers |
| source | 1..26 |
| | mol_type = other DNA |
| | organism = synthetic construct |

SEQUENCE: 5
```
gctggaggca agcgccataa tctgag                                         26
```

| SEQ ID NO: 6 | moltype = DNA length = 25 |
| --- | --- |
| FEATURE | Location/Qualifiers |
| source | 1..25 |
| | mol_type = other DNA |
| | organism = synthetic construct |

SEQUENCE: 6
```
gtgatcctga agctggtttc ttgag                                          25
```

| SEQ ID NO: 7 | moltype = DNA length = 23 |
| --- | --- |
| FEATURE | Location/Qualifiers |
| source | 1..23 |
| | mol_type = other DNA |
| | organism = synthetic construct |

SEQUENCE: 7
```
tcgccttccg actaggtgaa gag                                            23
```

| SEQ ID NO: 8 | moltype = DNA length = 24 |
| --- | --- |
| FEATURE | Location/Qualifiers |
| source | 1..24 |
| | mol_type = other DNA |
| | organism = synthetic construct |

SEQUENCE: 8
```
acctgttgtc cagttgcact tcgc                                           24
```